US00PP19140P3

(12) United States Plant Patent
Meilland

(10) Patent No.: US PP19,140 P3
(45) Date of Patent: Aug. 26, 2008

(54) HYBRID TEA ROSE PLANT NAMED 'MEIMARKIZE'

(50) Latin Name: *Rosa hybrida/Hybrid Tea Rose Plant*
Varietal Denomination: cv. Meimarkize

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 11/819,416

(22) Filed: Jun. 27, 2007

(65) Prior Publication Data

US 2008/0155720 P1 Jun. 26, 2008

(30) Foreign Application Priority Data

Dec. 26, 2006 (JP) ..... 20493

(51) Int. Cl.
*A01H 5/00* (2006.01)

(52) U.S. Cl. ..... Plt./134

(58) Field of Classification Search ..... Plt./134
See application file for complete search history.

(56) References Cited

U.S. PATENT DOCUMENTS

PP5,607 P * 12/1985 Meilland ..... Plt./137

* cited by examiner

*Primary Examiner*—Wendy C. Haas
(74) *Attorney, Agent, or Firm*—Buchanan Ingersoll & Rooney PC

(57) ABSTRACT

A new and distinct variety of Hybrid Tea rose plant is provided that forms at mid-season abundantly and substantially continuously attractive yellow-green blossoms suffused with pink processing a light fragrance wherein the numerous petals are positioned in a quartered manner. The buds are substantially globular-shaped. The vegetation is strong and attractive green foliage is formed. The plant forces well and is particularly well suited for cut flower production under greenhouse growing conditions.

1 Drawing Sheet

Botanical/commercial classification: *Rosa hybrida*/Hybrid Tea Rose Plant.
Varietal denomination: cv. Meimarkize.

SUMMARY OF THE INVENTION

The new variety of *Rosa hybrida* Hybrid Tea rose plant was created by artificial pollination wherein two parents were crossed which previously had been studied in the hope that they would contribute the desired characteristics. The female parent (i.e., the seed parent) was the 'Meisatex' variety (non patented in the United States). The male parent (i.e., the pollen parent) was the product of the cross of the 'Meikola' variety (U.S. Plant Pat. No. 5,607) and the 'Keidargo' variety (non-patented in the United States).

'Meisatex'×('Meikola'×'Keidargo').

The seeds resulting from the above pollination were sown and small plants were obtained which were physically and biologically different from each other. Selective study resulted in the identification of a single plant of the new variety.

It was found that the new Hybrid Tea rose plant of the present invention:

(a) forms strong vegetation, (b) forms substantially globular-shaped buds, (c) forms at mid-season abundantly and substantially continuously attractive yellow-green blossoms suffused with pink possessing a light fragrance wherein the numerous petals are positioned in a quartered manner, (d) displays attractive green foliage, (e) forces well under greenhouse growing conditions, and (f) is particularly well suited for cut flower production under greenhouse growing conditions.

The new variety well meets the needs of the horticultural industry and performs well under greenhouse growing conditions. No disease problem has been observed during observations to date when the new variety was being grown in greenhouses.

The new variety can be readily distinguished from its ancestors. For instance, the blossom coloration is considerably different from that of the 'Meisatex', 'Meikola', and 'Keidargo' varieties. More specifically, the 'Meisatex' variety forms orange-red blossoms, the 'Meikola' variety forms Venetian pink blossoms, and the 'Keidargo' variety forms dark red blossoms.

The new variety has been found to undergo asexual propagation in France by a number of routes, including budding, grafting, and the use of cuttings. Asexual propagation by the above-mentioned techniques in France has shown that the characteristics of the new variety are stable and are strictly transmissible by such asexual propagation from one generation to another.

The new variety has been named 'Meimarkize'.

BRIEF DESCRIPTION OF THE PHOTOGRAPH

The accompanying photograph shows that as nearly true as it is reasonably possible to make the same, in a color illustration of this character, typical specimens of the plant parts of the new variety. The rose plants of the new variety were approximately one year of age and were observed during May while growing on *Rosa indicia Major* understock and growing in greenhouses at Le Cannet des Maures, Var, France. Dimensions in centimeters are indicated at the bottom of the photograph, as is a standard color comparison.

Figures 1, 2, 3, 4, 5, 6, 7, 8, 9, 10, 11, 12, 13, 14, 15, 16:
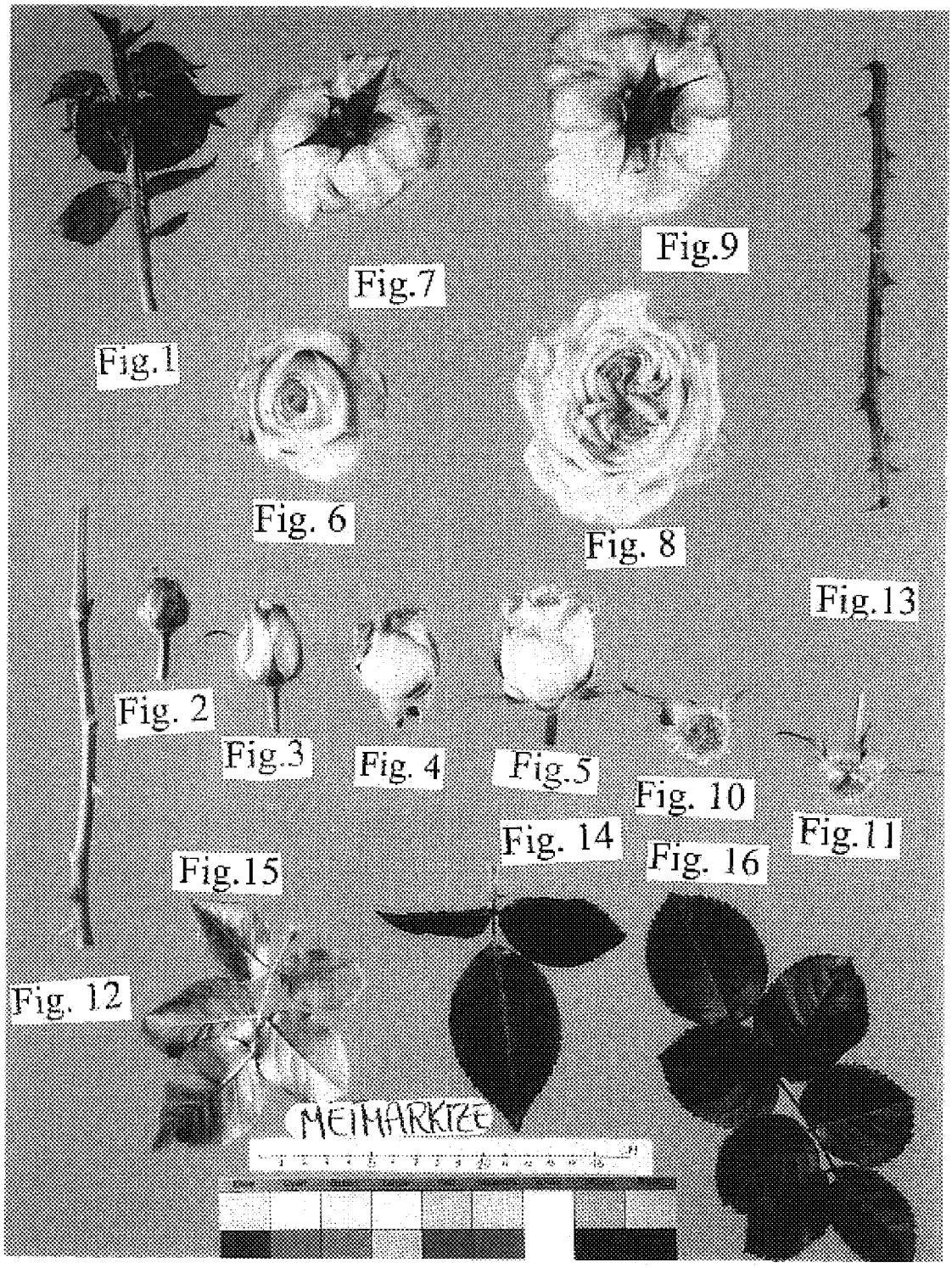
FIG. 1 illustrates a specimen of a young shoot.
FIG. 2 illustrates a specimen of a floral bud before the opening of the sepals.
FIG. 3 illustrates a specimen of a floral bud at the opening of the sepals.

FIG. 4 illsutrates a specimen of a floral bud at the opening of the petals;

FIG. 5 illustrates a specimen of a flower in the course of opening;

FIG. 6 illustrates a specimen of an open flower— plan view— obverse;

FIG. 7 illustrates a specimen of an open flower— plan view— reverse;

FIG. 8 illustrates a specimen of a fully open flower— plan view— obverse;

FIG. 9 illustrates a specimen of a fully open flower— plan view— reverse;

FIG. 10 illustrates a specimen of a floral receptacle showing the arrangement of the stamens and pistils;

FIG. 11 illustrates a specimen of a floral receptacle showing the arrangement of the pistils (stamens removed);

FIG. 12 illustrates a specimen of a flowering stem;

FIG. 13 illustrates a specimen of a main branch;

FIG. 14 illustrates a specimen of a leaf with three leaflets— plan view— upper surface;

FIG. 15 illustrates a specimen of a leaf with five leaflets— plan view— under surface; and FIG. 16 illustrates a specimen of a leaf with seven leaflets— plan view— upper surface.

DETAILED DESCRIPTION

The chart used in the identification of the colors in that of The Royal Horticultural Society (R.H.S. Colour Chart). The description is based on the observation of one-year-old plants during May which were budded on *Rosa indicia Major* understock and growing in greenhouses at Le Cannet des Maures, Var, France.

Class: Hybrid Tea.

Plant:

*Height.*—When pruned to a height of 0.85 cm, floral stems having lengths of approximately 60 to 70 cm on average are produced.

*Width.*—Approximately 80 cm on average.

Branches:

*Color.*—Young stems: near Yellow-Green Group 144A. Adult wood: near Green Group 143A.

*Thorns.*—On young stems: Small Prickles: Quantity: none. Long prickles: Quantity: none. On adult stem: Small prickles: Quantity: Approximately 10 on average on a stem length of 10 cm. Length: approximately 0.2 cm. average. Color: near Greyed-Yellow Group 160D with some Greyed-Orange Group 166A. Base: Obovate. Long prickles: Configuration: rather slightly, very longish pointed and curved downwards on the upper surface, and concave on the under surface. Quantity: approximately 1 on average on a stem length of 10 cm. Length: approximately 0.4 cm on average. Color: near Yellow-Green Group 160D with Greyed-orange Group 166A. Base: obovate.

Leaves:

*Stipules.*—Adnate, pectinate and narrow, smooth, approximately 1.8 cm in length on average, approximately 0.2 cm in width on average, near Green Group 138A no the upper side, and near Green Group 138B on the under surface.

*Petioles.*—Upper surface: near Green Group 143A in coloration. Under surface: near Green Group. 143B in coloration. Length: approximately 2.8 cm for the terminal leaflet.

*Rachis.*—Upper surface: Near Green Group 143A in coloration. Under surface: near Green Group 143B in coloration.

*Leaflets.*—Number: 3, 5 and 7 (most often). Shape: generally elliptical with a pointed tip and an obtuse base. Size: the terminal leaflet commonly are approximately 9.6 cm in length on average and approximately 5 cm in width on average. Serration: small and single (as illustrated). Texture: physically firm and thick. Color (young foliage): Upper surface: near Green Group 138A. Under surface: near Green Group 136B. Color (adult foliage): Upper surface: near Green Group 139A. Under surface: near Green Group 138B.

Inflorescence:

*Number of flowers.*—Commonly approximately 5 to 7 blossoms per stem.

*Peduncle.*—Smooth, approximately 2.5 cm in length on average, approximately 0.6 cm in diameter on average, and near Yellow-Green Group 144A in coloration.

*Sepals.*—Upper surface: smooth and near Yellow-Green Group 146B in coloration. Under surface: glandular and near Yellow-Green Group 144A in coloration.

*Size.*—Approximately 3.6 cm in length on average, and approximately 1.2 cm in width at the widest point on average. Shape: longish-pointed and new at the top and somewhat straight at the base. Extensions: two sepals commonly possess no extensions and three sepals commonly possess very weak extensions.

*Buds.*—Shape: substantially globular. Size: medium. Length: approximately 3 cm on average. Width: approximately 2.3 cm on average. Color as calyx breaks: Upper surface: near Red Group 56C, and amply suffused with near Red group 49A, and with a spot at the base of the near Green-Yellow Group 1C. Under surface: near Red Group 56C, and amply suffused with Red Group 49A and margined with Red Group 54A, and with a spot at the base of near Green-Yellow Group 1C more or less suffused with Yellow-Green Group 149A.

*Flower.*—Shape: cup-shaped. Diameter: approximately 8 cm on average. Color (in the course of opening): Upper surface: near Red Group 56C suffused with near Red Group 49A. Under surface: near Red Group 56C suffused with near Red Group 49A and more or less margined with Red Group 54A. Spot at base: near Green-Yellow Group 1C on both surfaces. Upper side: possesses external whorls of near Red Group 56C and 56D, and internal whorls of near Red Group 56C and 56D, more or less suffused with Red Group 49A. Under surface: near Yellow-Green 150D with suffused with Yellow-Green Group 144B and 144D on the external petals. External whorls are near Green-Yellow Group 1C margined with near Red Group 56C, and internal whorls are near Green-Yellow Group 1C and one more or less suffused with near Red Group 56C and near Red Group 49A. Spot at base: bear Green-Yellow Group 1A. Color stability: slight change with age. Fragrance: light. Lasting quality: the blossoms commonly last approximately 14 to 16 days on the plant on average, and approximately 9 or 10 days on average when cut and placed in a vase. Petal number: approximately 97 on average under normal growing conditions. Petal shape: with a substantially rounded tip and base. Petal texture: consistent and somewhat firm. Petal length: approximately 5.4 cm on average. Petal width: approximately 5.7 cm on average. Petal arrangement: imbricated, without petaloids, and commonly quartered. Petal drop: good with the petals commonly detaching cleanly before drying. Stamen number: approximately 57 on average. Anthers: regularly arranged around the styles, approximately 0.3 cm in size on average, and near Orange Group 26B in coloration. Pollen: present. Filaments: approximately 0.5 cm in length on average and near Group 1A in coloration. Pistils: approximately 172 on average. Stigmas: approximately 0.8 cm in size on average and near Green-Yellow Group 1D in coloration. Styles: approximately 0.1 cm in length on average, and near Red-Purple Group 58A in coloration. Receptacle: smooth, funnel-shaped in longitudinal section, approximately 1.5 cm in length on average, approximately 1.7 cm in width on average at the widest point, and near Yellow-Green Group 144A in coloration. Hips: none observed to date when grown under greenhouse growing conditions.

Development:

*Vegetation.*—Strong.

*Blooming.*—Mid-season, abundant and substantially continuous.

*Tolerance to diseases.*—No diseases have been observed during observations to date when grown in greenhouses.

*Aptitude to bear fruit.*—None observed during observations to date.

*Aptitude to to forcing.*—Good.

I claim:

1. A new and distinct Hybrid Tea rose plant characterized by the following characteristics:

(a) forms strong vegetation, (b) forms substantially globular-shaped buds, (c) forms at mid-season abundantly and substantially continuously attractive yellow-green blossoms suffused with pink possessing a light fragrance wherein the numerous petals are positioned in a quartered manner, (d) displays attractive green foliage, (e) forces well under greenhouse growing conditions, and (f) is particularly well suited for cut flower production under greenhouse growing conditions;

substantially as shown and described.

* * * * *

MEIMARKIZE